(12) United States Patent
Librot et al.

(10) Patent No.: US 8,740,911 B2
(45) Date of Patent: Jun. 3, 2014

(54) METHOD OF PREPARING A FEMUR FOR IMPLANTATION OF A FEMORAL IMPLANT

(75) Inventors: Daniel Librot, Hoboken, NJ (US);
Christopher Pawlak, Hoboken, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1182 days.

(21) Appl. No.: 12/291,340

(22) Filed: Nov. 7, 2008

(65) Prior Publication Data

US 2010/0121389 A1 May 13, 2010

(51) Int. Cl.
*A61B 17/58* (2006.01)

(52) U.S. Cl.
USPC ............ 606/88; 606/86 R; 606/96; 623/20.14

(58) Field of Classification Search
USPC ......... 606/86 R, 87, 88, 96; 623/20.14–20.36
See application file for complete search history.

(56) References Cited

U.S. PATENT DOCUMENTS

| | | | |
|---|---|---|---|
| 4,653,486 A | 3/1987 | Coker | |
| 4,653,488 A | 3/1987 | Kenna et al. | |
| 4,721,104 A * | 1/1988 | Kaufman et al. | ............... 606/88 |
| 5,112,331 A | 5/1992 | Miletich | |
| 5,122,144 A | 6/1992 | Bert et al. | |
| 5,147,367 A | 9/1992 | Ellis | |
| 5,203,784 A | 4/1993 | Ross et al. | |
| 5,234,433 A | 8/1993 | Bert et al. | |
| 5,257,996 A | 11/1993 | McGuire | |
| 5,458,608 A | 10/1995 | Wortrich | |
| 5,562,671 A | 10/1996 | Goble et al. | |
| 5,578,039 A | 11/1996 | Vendrely et al. | |
| 5,628,749 A | 5/1997 | Vendrely et al. | |
| 5,667,511 A | 9/1997 | Vendrely et al. | |
| 5,669,912 A | 9/1997 | Spetzler | |
| 5,672,178 A | 9/1997 | Petersen | |
| 5,776,201 A * | 7/1998 | Colleran et al. | ........... 623/20.15 |
| 5,976,147 A | 11/1999 | LaSalle et al. | |
| 5,980,558 A | 11/1999 | Wiley | |
| 6,322,563 B1 | 11/2001 | Cummings et al. | |
| 6,379,364 B1 * | 4/2002 | Brace et al. | ..................... 606/96 |
| 6,395,007 B1 | 5/2002 | Bhatnagar et al. | |
| 6,517,546 B2 | 2/2003 | Whittaker et al. | |
| 6,554,838 B2 | 4/2003 | McGovern et al. | |
| 6,623,488 B1 | 9/2003 | Leone, Jr. | |
| 6,645,214 B2 | 11/2003 | Brown et al. | |
| 6,770,079 B2 | 8/2004 | Bhatnagar et al. | |
| 6,887,246 B2 | 5/2005 | Bhatnagar et al. | |
| 6,942,670 B2 | 9/2005 | Heldreth et al. | |
| 6,958,067 B2 | 10/2005 | Whittaker et al. | |
| 7,066,943 B2 * | 6/2006 | Zirkle, Jr. | ....................... 606/98 |
| 2002/0082607 A1 | 6/2002 | Heldreth et al. | |

(Continued)

*Primary Examiner* — Cris L Rodriguez
*Assistant Examiner* — Edward Moran
(74) *Attorney, Agent, or Firm* — Lerner, David, Littenberg, Krumholz & Menlik, LLP (57) ABSTRACT

A method of preparing a distal femur for implantation of a femoral implant is described. The distal femur is resected to accommodate placement of a trial implant thereon. The trial implant is then placed against the resected distal femur to locate an optimal position for the femoral implant. The trial implant comprises one or more apertures through which holes are drilled in the distal femur and into which trial pegs are inserted into the distal femur to secure the trial implant to the distal femur. The surgeon then evaluates whether the holes in the femur are located appropriately to securely implant the femoral implant onto the femur. The trial implant is ultimately removed in favor of a final implant.

20 Claims, 9 Drawing Sheets

(56) References Cited

U.S. PATENT DOCUMENTS

| | | |
|---|---|---|
| 2002/0143340 A1 | 10/2002 | Kaneko |
| 2003/0093080 A1 | 5/2003 | Brown et al. |
| 2004/0153087 A1* | 8/2004 | Sanford et al. ............ 606/88 |
| 2004/0215203 A1 | 10/2004 | Michelson |
| 2006/0173463 A1* | 8/2006 | Dees ............ 606/88 |
| 2006/0184176 A1 | 8/2006 | Straszheim-Morley et al. |
| 2006/0217734 A1* | 9/2006 | Sanford et al. ............ 606/88 |
| 2006/0235421 A1* | 10/2006 | Rosa et al. ............ 606/88 |
| 2007/0288027 A1 | 12/2007 | Grafton et al. |
| 2008/0019798 A1 | 1/2008 | Lee |

\* cited by examiner

METHOD OF PREPARING A FEMUR FOR IMPLANTATION OF A FEMORAL IMPLANT

BACKGROUND OF THE INVENTION

The human knee joint is a hinge joint formed by the cooperation of the distal end of the femur and the proximal end of the tibia, as well as the cooperation of various tendons, ligaments, and cartilage surfaces with each other and/or the femur and tibia. Because of its natural anatomical configuration and the constant pressure it is put under, the knee joint is highly susceptible to the development of defects, whether caused by injury or natural wear and tear. These defects can cause long-term or even permanent pain to patients. Often times, a person suffering from such ailments will be unable to put much, or in some cases, any, weight on the injured knee, making it difficult or impossible to walk. As such, many surgical procedures have been developed to repair defects of the knee joint.

One type of knee ailment, which can result from trauma to the knee or from natural wear and tear, is the deterioration or other damage of the cartilage located on one or both of the femoral condyles. This cartilage provides an articulation surface that allows for the fluid movement of the distal end of the femur and the proximal end of the tibia (which also includes cartilage surfaces) with respect to each other. Cartilage defects may result on one or both femoral condyles. In the case of the former, unicondylar knee procedures have been developed to replace the cartilage surfaces (and portions of bone) on the single femoral condyle and corresponding cartilage surface (and portions of bone) of the tibia. In the case of the latter, total knee procedures have been developed to replace the cartilage surfaces (and portions of bone) on both femoral condyles and corresponding cartilage surfaces (and portions of bone) of the tibia.

Both unicondylar and total procedures involve the resection of at least one of the condyles of the femur to accept a femoral implant and the portion of the tibia corresponding to the femoral condyle(s) to accept a tibial implant. These implants are designed to replicate the articular surfaces formed by the original anatomy. Of course, depending upon patient size and/or other anatomical features, the size, location, and orientation of the femoral and tibial implants may widely vary. As such, much care must be given to properly implanting the implants so that the natural movement of the knee joint is restored. To aid in achieving this goal, trial implants, which essentially amount to provisional versions of the final implants, are often utilized. In addition to the tools utilized in making the bone cuts and for use in implanting the final implants, tools are often required to place the trial implants. The overwhelming number of implants, trial implants and tools required or desirable for a single knee surgery necessarily increases costs and overall time associated with the surgery.

Therefore, there is a need for an effective way of properly preparing the distal femur and proximal tibia to receive implants during a surgical knee procedure, through the use of less implants and tools.

SUMMARY OF THE INVENTION

A user prepares a distal femur for implantation of a femoral implant by resecting a condyle of the distal femur and placing a trial femoral implant with at least one aperture against the resections. The user then inserts a pin into the femur through a pin aperture of the trial implant to hold the trial implant in place. Using a drill guide and drilling apparatus, the user then drills trial peg holes into the femur through the drill guide and the apertures in the trial implant. The user then uses an insertion tool to couple with a trial peg and insert the trial peg into a trial peg hole of the femur through an aperture of the trial implant to secure the implant to the femur. The user then removes the pin from the femur and the trial implant. The user then tests the mobility of the knee joint with the trial implant in place to verify whether the size, position, and orientation of the trial implant are appropriate for a femoral implant. Next, the user uses the insertion tool to remove the trial peg from the femur and the trial implant, and then removes the trial implant from the femur.

Based on the user's verification whether the size, position, and orientation of the trial implant were appropriate for a femoral implant, the user either implants a femoral implant at the same position and orientation, or revaluates the knee joint. The latter may include beginning the process again with a new trial implant and may involve the re-drilling of larger peg holes in the femur.

A first aspect of the present invention is a method of preparing a distal femur for implantation of a femoral implant. In accordance with certain embodiments of this first aspect, the method includes the steps of making at least one resection in the distal femur, selecting a trial femoral implant to be implanted on the distal femur, the trial implant including a first aperture, placing the trial implant on the resected distal femur, drilling a first peg hole in the femur through the first aperture, and inserting a trial peg through the first aperture and into the first peg hole formed in the distal femur.

In other embodiments, the method may include the further step of drilling a second peg hole in the femur through a second aperture in the trial implant. The drilling step may include drilling through a drill guide placed adjacent the first aperture, with the drill guide including an elongate tube having a passage aligned with the first aperture. The first aperture may include a countersink and a shoulder, the elongate tube placed within the countersink and against the shoulder. The drilling step may include drilling through a drill guide placed adjacent the first and second apertures. Alternatively, or additionally, the drill guide may include a first elongate tube having a first passage aligned with the first aperture and a second elongate tube having a second passage aligned with the second aperture. The inserting step may include coupling and uncoupling the trial peg with an insertion device. The method may include the further step of removing the trial peg from the distal femur, where the removing step includes coupling the trial peg with an insertion device. The method may also include the step of verifying the position and orientation of the trial implant on the distal femur. The method may also include the step of removing the trial implant from the femur and implanting a femoral implant having a first peg, the first peg disposed in the first peg hole when the femoral implant is implanted. The trial peg may include a head and a shank and the first aperture may include a countersink and shoulder, where the head of the trial peg is smaller than the countersink and larger than the shoulder. The method may also include the step of evaluating the spacing of a knee joint, where the evaluating step includes contacting and moving the trial femoral implant with a tibial trial implant.

A second aspect of the present invention is another method of preparing a distal femur for implantation of a femoral implant. In accordance with one embodiment of this second aspect, the method may include the steps of making at least one resection in the distal femur, selecting a trial femoral implant to be implanted on the distal femur, the trial implant including a first aperture having a first countersink and a first shoulder, placing the trial implant on the resected distal femur, placing a drill guide in the first countersink of the first aperture, drilling a first peg hole in the femur through the drill guide and the first aperture, and inserting a trial peg through the first aperture and into the first peg hole formed in the distal femur, the trial peg including a head dimensioned smaller than the first countersink and larger than the first shoulder and a shank dimensioned smaller than the first countersink and first shoulder.

BRIEF DESCRIPTION OF THE DRAWINGS

A more complete appreciation of the subject matter of the present invention and the various advantages thereof can be realized by reference to the following detailed description with reference to the accompanying drawings in which.

DETAILED DESCRIPTION

In describing the preferred embodiments of the subject matter illustrated and to be described with respect to the drawings, specific terminology will be used for the sake of clarity. However, the invention is not to be limited to the specific term so selected, and it is to be understood that each specific term includes all technical equivalents which function or operate in a similar manner to accomplish a similar purpose. Furthermore, it is noted that while the methods and apparatus of the present invention are shown and described in connection with a unicondylar procedure, such may also apply to a total knee procedure.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
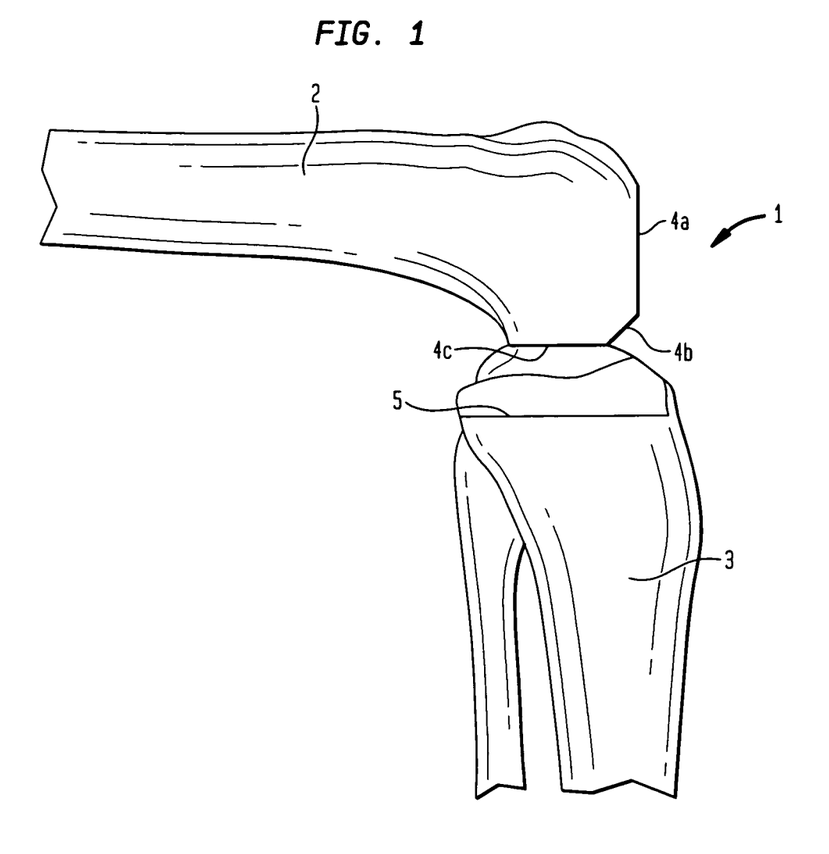
FIG. 1 is a side perspective view of the bones of a knee joint with resections made on both the distal femur and proximal tibia.

FIG. 1 depicts a knee joint 1 which has been prepared, so that both a distal portion of a femur 2 and a proximal portion of a tibia 3 of knee joint 1 have been resected in accordance with conventional surgical techniques for a unicondylar knee procedure. Specifically, the distal portion of one condyle of femur 2 has been resected to create resected surfaces 4a-c and the proximal portion of one side of tibial 3 has been resected to create a single flat resected surface 5. Resected surfaces 4a-c are configured to accept and engage with like surfaces formed on a final femoral implant (as well as a trial femoral implant), and resected surface 5 is configured to accept and engage with a like surface formed on a final tibial implant (as well as a trial tibial implant). Different implants may require cooperation with differently configured resected surfaces on the femur and/or tibia. For instance, it is contemplated that a final femoral implant (and trial femoral implant) may be configured to engage five resected surfaces on the distal portion of femur 2, as opposed to the three shown in FIG. 1. Likewise, although the resected surfaces are shown in the accompanying drawings as being flat, such surfaces may be of any configuration, including but not limited to curved surfaces. Moreover, although the resected surfaces are shown in the drawings as being formed in the actual bone of the femur and tibia, it is contemplated that such surfaces could be formed in cartilage surfaces in the knee joint. It is to be understood that the present invention is not limited to only those configurations shown and/or discussed in the present application.

Figure 2:
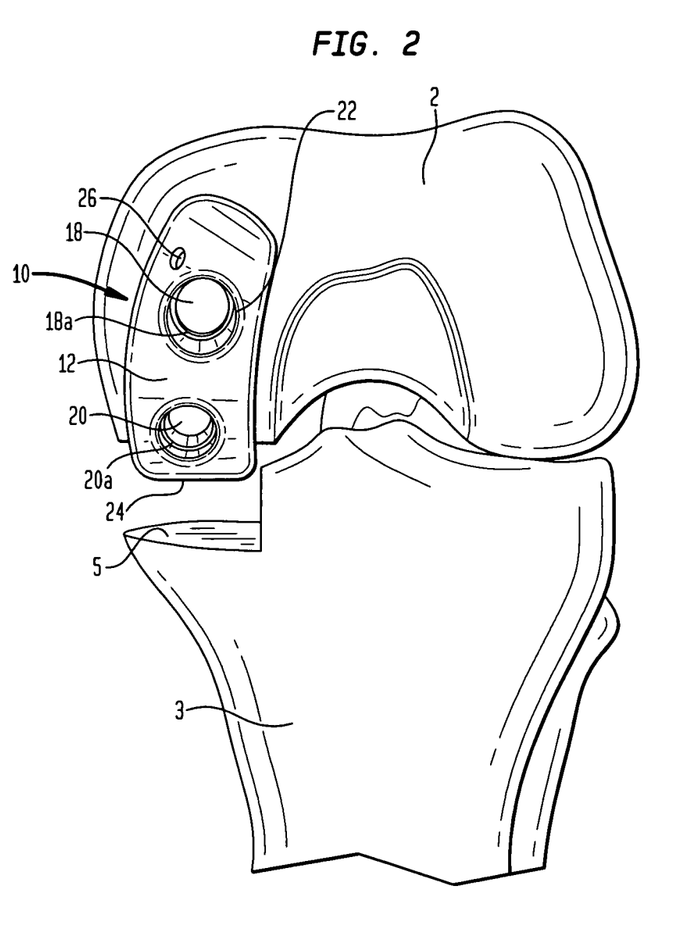
FIG. 2 is a front perspective view of the knee joint shown in FIG. 1 with a trial femoral implant placed on the distal femur.
Figure 3:
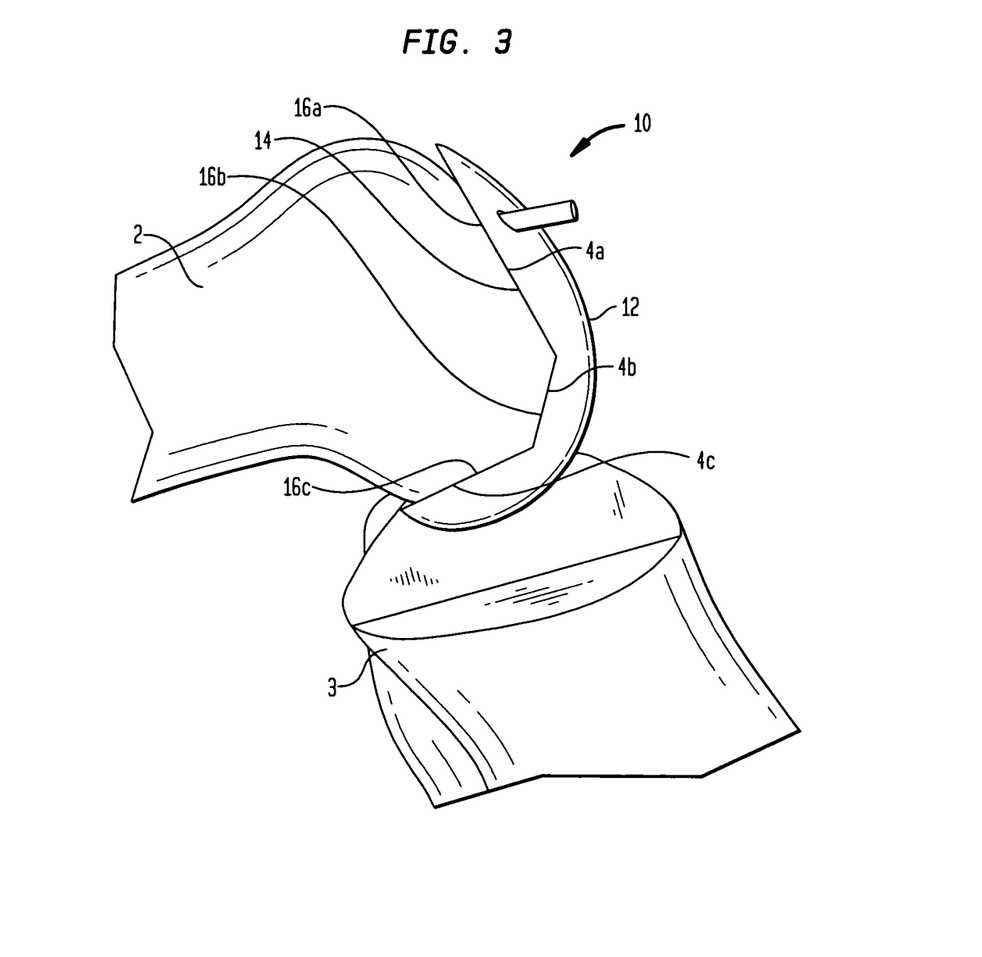
FIG. 3 is a side perspective view of the knee joint shown in FIG. 2.

FIGS. 2 and 3 show a femoral trial implant 10 in accordance with the present invention. Specifically, trial implant 10 is shown placed on the resected distal portion of femur 2 depicted in FIG. 1. Trial implant 10 includes an articular surface 12 and an opposing bone contacting surface 14 (best shown in FIG. 3). While articular surface 12 is a generally continuous curved surface, bone contacting surface is made up of three intersecting flat surfaces 16a, 16b, and 16c which cooperate with resected surfaces 4a, 4b, and 4c, respectively. Trial implant 10 also includes apertures 18 and 20, which are formed through articular surface 12 and bone contacting surface 14 so as to allow for access to femur 2 while the implant is placed on the bone. Preferably, aperture 18 includes a countersunk surface 18a and aperture 20 includes a countersunk surface 20a, thereby forming shoulders 22 and 24, respectively. In the embodiment shown in the figures, trial implant 10 further includes a pin aperture 26 (best shown in FIG. 2) to allow insertion of a pin 28 (best shown in FIG. 4) into femur 2 to temporarily hold trial implant 10 in place.

Figure 4:
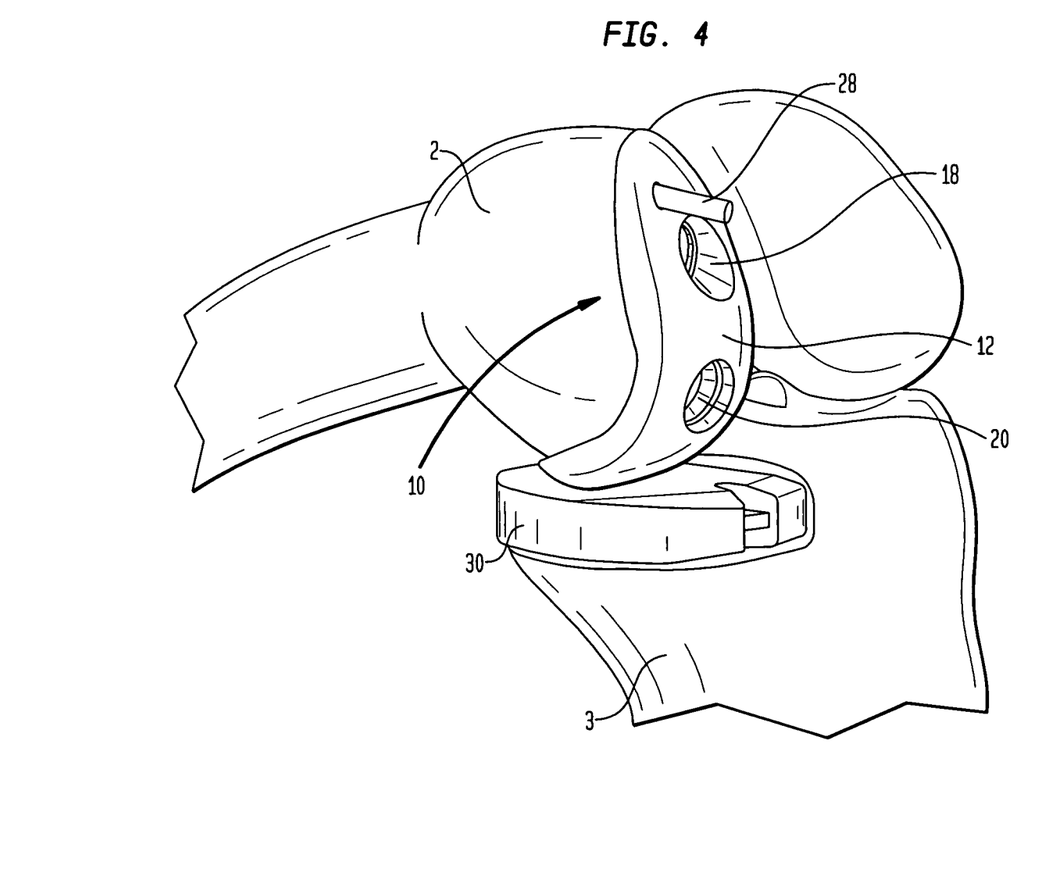
FIG. 4 is a perspective view of the knee joint shown in FIG. 1 with trial implants placed on both the distal femur and proximal tibia.
Figure 9:
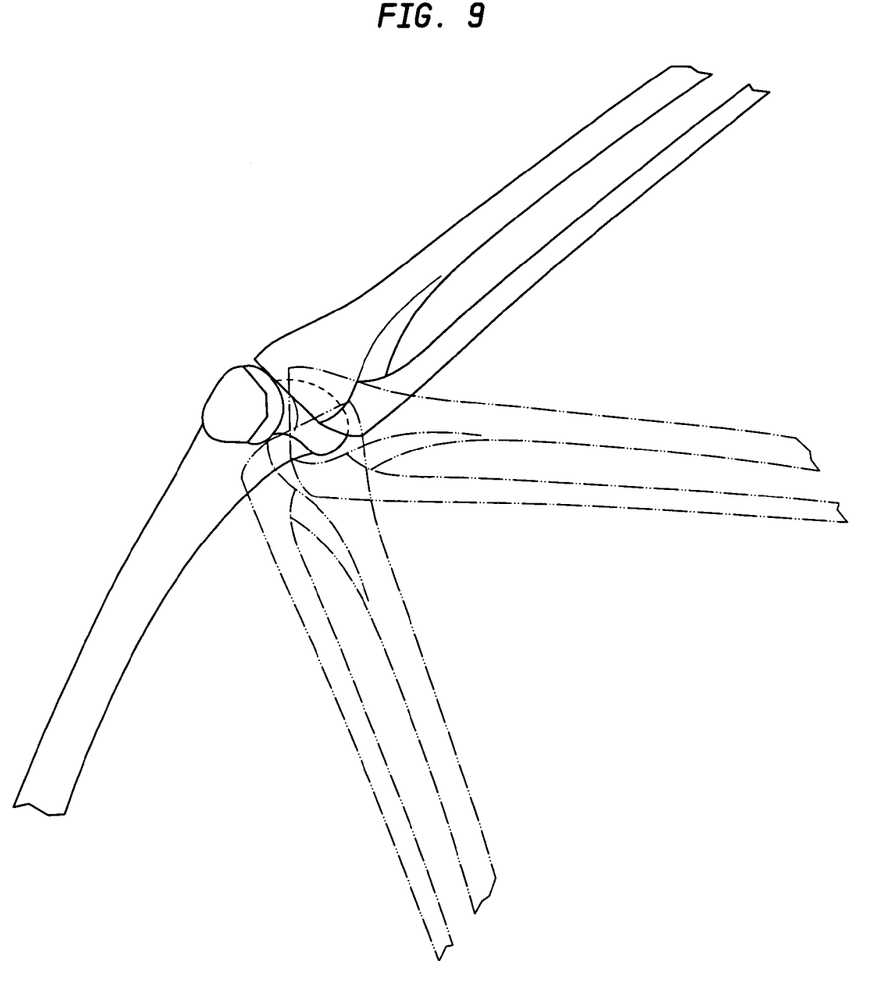
FIG. 9 is a side perspective illustration of the bones of the knee joint with trial implants placed on both the distal femur and proximal tibia and the range of motion of the joint being tested.
Figure 10:
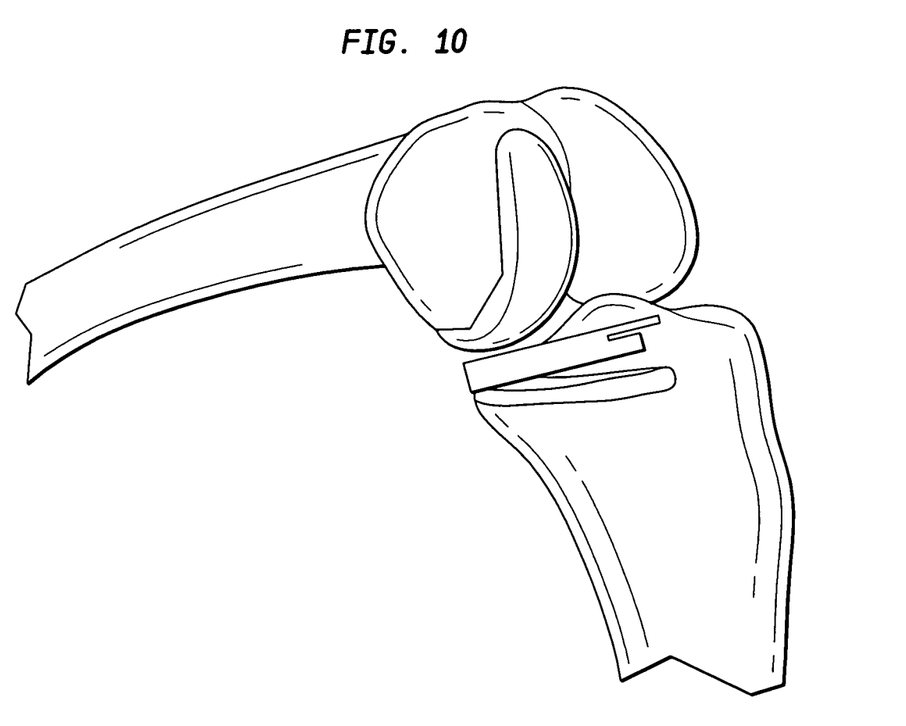
FIG. 10 is a perspective view similar to that of FIG. 4 with a final femoral implant and final tibial implant implanted on the distal femur and proximal tibia, respectively.

Similar to FIGS. 2 and 3, FIG. 4 depicts trial implant 10 placed on the resected distal portion of femur 2. Pin 28 is placed through pin aperture 26 so as to hold trial implant 10 in place during drilling procedures that will be discussed more fully below. FIG. 4 also depicts a tibial trial implant 30 placed on resected surface 5 of tibia 3. Any suitable tibial trial implant can be used in connection with the present invention. As will be discussed more fully below, implants 10 and 30 are meant to emulate final implants (shown in FIG. 10) that are implanted during the surgical procedure, but are provided to allow the surgeon to confirm the size and fit of the final implants and evaluate the movement of the femur and tibia with respect to each other prior to final implantation (see FIG. 9). As will be discussed more fully below, trial implant 10 is also provided to allow for further preparation of femur 2.

The placement of a final femoral implant requires that such be fixed to femur 2 in some fashion. In accordance with the present invention, it is contemplated to utilize an implant having two pegs meant to engage holes formed in the distal portion of femur 2. These holes are preferably formed prior to the implantation of the final implant, through the use of trial implant 10 of the present invention. Specifically, aforementioned apertures 18 and 20 are meant to cooperate with a drill guide 32 (best shown in FIG. 5) to guide a drill 34 to prepare holes in the distal femur 2. Apertures 18 and 20 are essentially sized and configured on implant 10 so as to directly correspond to the peg of the final femoral implant. Likewise, drill guide 32 includes two elongate drill tubes 36 and 38 which are sized and configured to fit within countersinks 18a and 20a and abut shoulders 22 and 24 of apertures 18 and 20. These tubes provide a guide for the elongate drill 34, which is utilized in making the two necessary peg holes in distal femur 2. Drill guide 32 also preferably includes an aperture 40 (shown as a third elongate tube in the drawings) that is capable of being removably coupled with an insertion/extraction tool 42 (discussed more fully below). It is noted here that drill guide 32 may include a single drill tube that would require the separate placement of the guide within apertures 18 and 20 to prepare the necessary peg holes. It is also noted that drill guide 32 may be formed integral with an insertion handle, or tool 42 may be left connected with drill guide 32 during a surgical procedure. However, the removable nature of tool 42 from drill guide 32 may allow for the tool to be removed prior to the drill procedure, thereby providing the surgeon with a clearer view of the surgical area.

Figure 5:
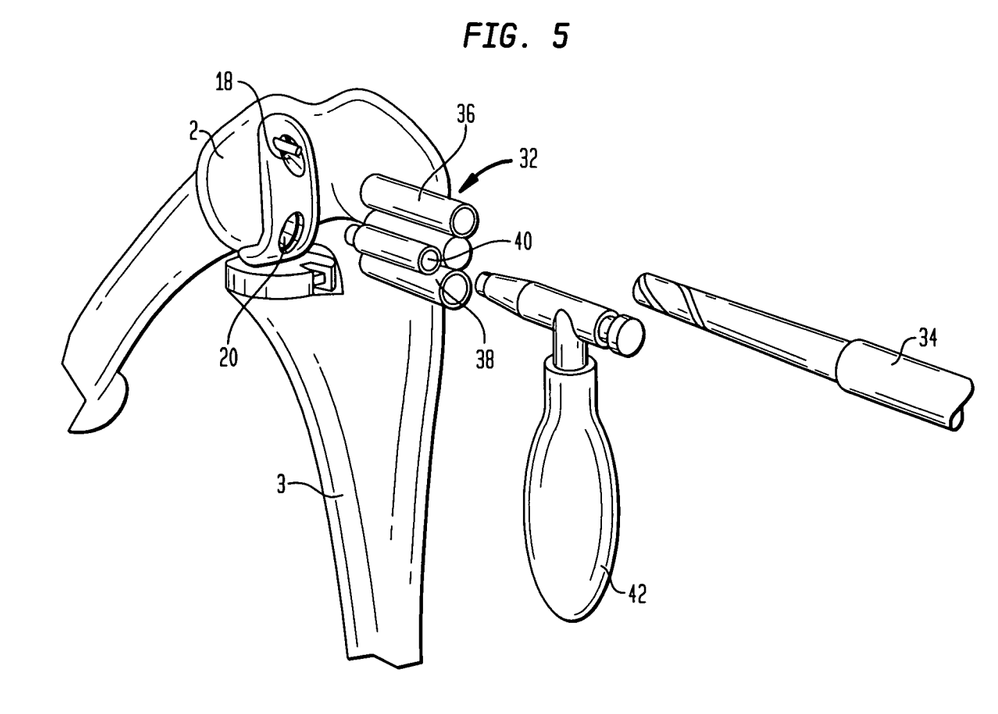
FIG. 5 is a perspective view similar to that of FIG. 4 with a drill guide, insertion tool used to place the drill guide, and a drilling apparatus for drilling through the drill guide and the trial femoral implant shown.

In use, after trial implant 10 is placed on the resected distal end of femur 2 (and optionally pinned by pin 28), drill guide 32 is engaged with insertion tool 42 and tubes 36 and 38 are guided into apertures 18 and 20, respectively. The tubes are preferably inserted until a portion of tube 36 abuts shoulder 22 and a portion of tube 38 abuts shoulder 24. Because the tubes are sized to be slightly smaller than countersinks 18a and 20a, they are somewhat retained within apertures 18 and 20. Thus, insertion/extraction tool 42 can be disengaged from guide 32. Alternatively, tool 42 can be left in place. Regardless, the surgeon can then move drill 34 through each of tubes 36 and 38 to form the peg holes discussed above. When complete, tool 42 can be re-engaged with drill guide 32 (if it had been previously disengaged) and the assembly can be removed from the surgical area. As trial implant 10 is designed to emulate a final implant, and apertures 18 and 20 are so situated, femur 2 is now provided with the necessary peg holes to accept pegs of a final implant.

Figure 6:
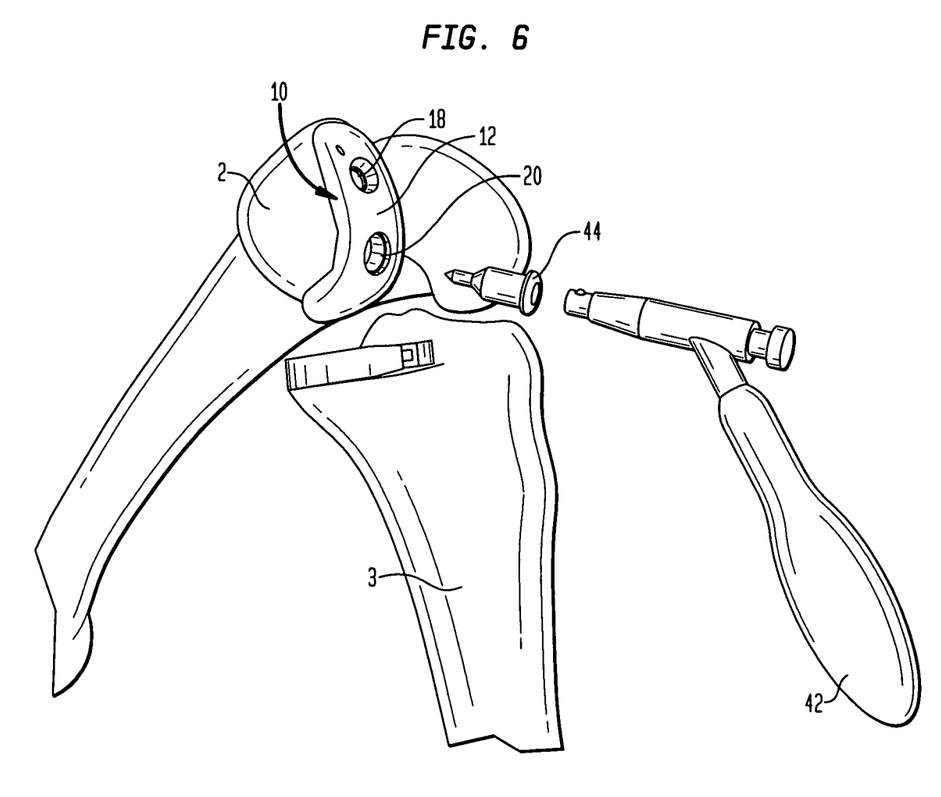
FIG. 6 is a perspective view similar to that of FIG. 4 with a pin and an insertion tool for inserting the pin into the femur through a pin aperture of the trial femoral implant shown.
Figure 7:
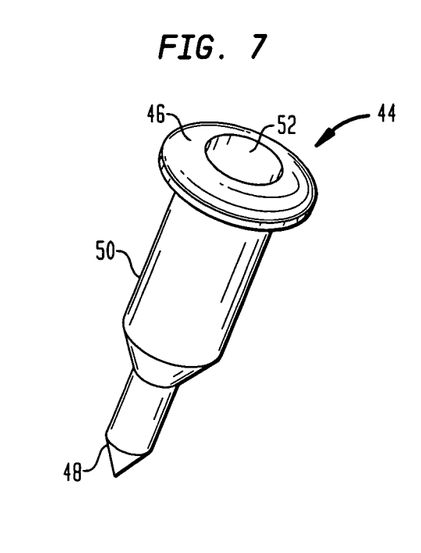
FIG. 7 is a perspective view of the pin shown in FIG. 6.

With the peg holes having been formed, the surgeon then utilizes trial implants 10 and 30 to evaluate the fit of the implants and the spacing of knee joint 1. However, because it extends from articular surface 12 of trial implant 10, pin 28 (if inserted) must be removed. In order to ensure that trial implant 10 remains attached to femur 2, it is affixed in another manner. As is shown in FIG. 6, in accordance with the present invention, a trial peg 44 is provided and is preferably capable of cooperating with insertion/extraction tool 42, or a similar tool. Trial peg 44 includes a head 46, an elongated spike 48, and a shank 50 connecting the head and the spike (shown in more detail in FIG. 7). Head 46 is preferably dimensioned to pass through countersink 20a, but abut shoulder 24. When placed within aperture 20, head therefore sits below articular surface 12. This allows the surgeon to move trials 10 and 30 with respect to each other without any interference from trial peg 44, or any other component. Spike 48 and shank 50 are preferably sized and configured to fit entirely through aperture 20 and the already prepared peg hole in femur 2. However, spike 48 preferably extends far enough from shank 50 to extend into bone situated below the already prepared peg hole, so as to allow the spike to engage unprepared bone in the femur 2. This allows trial peg to act to fix trial implant 10 to femur 2 much in the way a screw or nail would in a wood substrate. The trial peg also preferably includes an aperture 52 that extends through head 46 and partially into shank 50 for engagement with insertion tool 42. While discussed above as only being placed within aperture 20, it is noted that in other embodiments, peg 44 could be designed to be placed within aperture 18, or in both apertures.

In use, prior or subsequent to removing pin 28, trial peg 44 is coupled with insertion/extraction tool 42 which the surgeon utilizes to guide the peg through aperture 20 of implant 10. Trial peg 44 is pushed through aperture 20 until head 46 abuts shoulder 24 and spike 48 is inserted into some unprepared bone. The surgeon may perform this insertion merely by hand or could utilize an impaction instrument to ensure the pin is properly placed. With the peg so placed, tool 42 can be removed. The surgeon can then evaluate knee joint 1. This may include moving the implants 10 and 30 with respect to each other, so that the femur and tibia are moved through a full range of motion. The fact that trial peg 44 is completed disposed below articular surface 12 allows for this entire motion. When satisfied with the fit and movement of the joint, the surgeon can then re-engage tool 42 with trial peg 44 and remove the peg. Again, the surgeon may perform this step merely by hand or through the use of an additional instrument such as a grip or the like. Trial implants 10 and 30 can then be removed from knee joint 1 and the final implants can be implanted (see FIG. 10).

Figure 8:
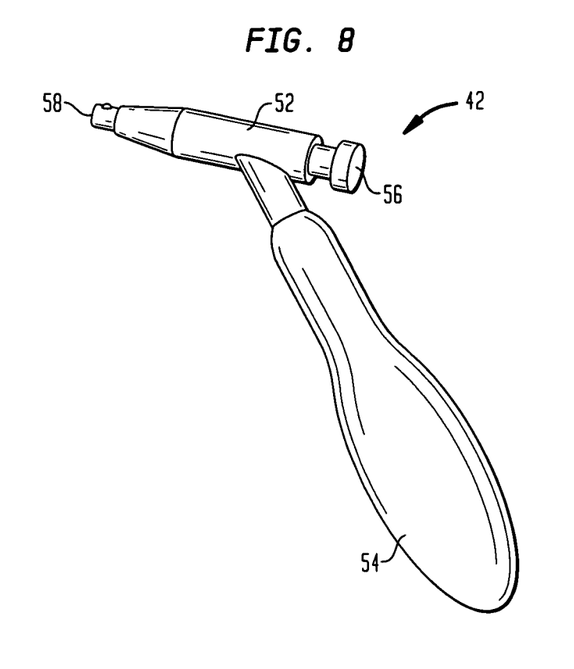
FIG. 8 is a perspective view of the insertion tool shown in FIGS. 5 and 6.

Insertion/extraction tool 42 is preferably meant to cooperate with both drill guide 32 and trial peg 44. While many different insertion/extraction tools can be utilized, with each using different methods to connect with guide 32 and peg 44, FIG. 8 illustrates in more detail one embodiment tool 42 in accordance with the present invention. The tool shown in that figure includes a barrel 52 and a handle 54 which are connected to each other. At one end of barrel 52 is an actuator 56 (shown as a depressible button), and at the other end is a spring detent tip 58. Tip 58 is preferably dimensioned to couple with both aperture 40 of drill guide 32 and aperture 52 of trial peg 44. Likewise, tip 58 preferably includes a spring detent meant to cooperate with a corresponding structure formed on drill guide 32 and trial peg 44. For instance, both drill guide 32 and trial peg 44 includes apertures formed near their respective tool engaging apertures for acceptance of a ball or other structure of the spring detent. In use, depression of actuator 56 causes the spring detent to move thereby allowing for the attachment and removal of tip 58 from either aperture 40 or aperture 52. Actuator 56 may be spring actuated so as to allow for the actuator to be biased in an engagement position absent a force applied thereto. It is also contemplated to provided one tool for use in inserting drill guide 32 and trial peg 44, and a separate tool for use in extracting such components. Moreover, specific tools may be provided for cooperation with only one of guide 32 and peg 44.

The description provided herein is intended to be exemplary, and the present invention is not limited to the embodiment disclosed herein. It is acknowledged that other embodiments or variations of the present embodiments will become obvious to those skilled in the art, and the present application intends to encompass all such embodiments. For example, while the present disclosure describes a trial implant including two trial peg holes for use with two trial pegs, a number of different quantities of pegs and peg holes could be used without deviating from the scope and spirit of the present invention. Similarly, although the present embodiment discloses a trial implant having three flat posterior surfaces and resections creating three surfaces for engagement therewith, a trial implant and resections having a different number of surfaces would not deviate from the scope and spirit of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing a distal femur for implantation of a femoral implant, comprising the steps of:
   making at least one resection in the distal femur;
   selecting a trial femoral implant to be implanted on the distal femur, the trial implant including a first aperture;
   placing the trial implant on the resected distal femur;
   drilling a first peg hole in the femur through the first aperture;
   inserting a trial peg through the first aperture and into the first peg hole formed in the distal femur;
   evaluating the spacing of a knee joint, including contacting and moving the trial femoral implant with respect to a tibial trial implant through a full range of motion while the trial peg is inserted through the first aperture and into the first peg hole formed in the distal femur;
   removing the trial peg from the distal femur;
   removing the trial implant from the femur; and
   implanting a femoral implant having a first peg, the first peg disposed in the first peg hole when the femoral implant is implanted.

2. The method as claimed in claim 1, further comprising the step of drilling a second peg hole in the femur through a second aperture in the trial implant.

3. The method as claimed in claim 1, wherein the drilling step includes drilling through a drill guide placed adjacent the first aperture.

4. The method as claimed in claim 3, wherein the drill guide includes an elongate tube having a passage aligned with the first aperture.

5. The method as claimed in claim 4, wherein the first aperture includes a countersink, the elongate tube placed within the countersink.

6. The method as claimed in claim 2, wherein the drilling steps include drilling through a drill guide placed adjacent the first and second apertures.

7. The method as claimed in claim 6, wherein the drill guide includes a first elongate tube having a first passage aligned with the first aperture and a second elongate tube having a second passage aligned with the second aperture.

8. The method as claimed in claim 1, wherein the inserting step includes coupling and uncoupling the trial peg with an insertion device.

9. The method as claimed in claim 1, wherein the removing the trial peg step includes coupling the trial peg with an insertion device.

10. The method as claimed in claim 1, further comprising the step of verifying the position and orientation of the trial implant on the distal femur.

11. The method as claimed in claim 1, wherein the trial peg includes a head and a shank.

12. The method as claimed in claim 11, wherein the first aperture includes a countersink and a shoulder.

13. The method as claimed in claim 12, wherein the head of the trial peg is smaller than the countersink and larger than the shoulder.

14. The method as claimed in claim 1, wherein the trial implant further includes a pin aperture, and wherein the placing step includes inserting a pin into the femur through the pin aperture.

15. The method as claimed in claim 14, further comprising the step of removing the pin from the distal femur after the step of inserting a trial peg.

16. The method as claimed in claim 1, wherein the femoral implant and the trial femoral implant are total implants.

17. The method as claimed in claim 1, wherein the femoral implant and the trial femoral implant are unicondylar implants.

18. A method of preparing a distal femur for implantation of a femoral implant, comprising the steps of:
   making at least one resection in the distal femur;
   selecting a trial femoral implant to be implanted on the distal femur, the trial implant including a first aperture having a first countersink and a first shoulder;
   placing the trial implant on the resected distal femur;
   placing a drill guide in the first countersink of the first aperture;
   drilling a first peg hole in the femur through the drill guide and the first aperture;
   inserting a trial peg through the first aperture and into the first peg hole formed in the distal femur, the trial peg including a head dimensioned smaller than the first countersink and larger than the first shoulder and a shank dimensioned smaller than the first countersink and first shoulder;
   evaluating the spacing of a knee joint, including moving the trial femoral implant and a tibial trial implant through a full range of motion while the trial peg is inserted through the first aperture and into the first peg hole formed in the distal femur;
   removing the trial peg from the distal femur;
   removing the trial implant from the femur; and
   implanting a femoral implant having a first peg, the first peg disposed in the first peg hole when the femoral implant is implanted.

19. The method as claimed in claim 18, wherein the femoral implant and the trial femoral implant are total implants.

20. The method as claimed in claim 18, wherein the femoral implant and the trial femoral implant are unicondylar implants.

* * * * *